United States Patent
Jin et al.

(10) Patent No.: US 6,884,610 B2
(45) Date of Patent: Apr. 26, 2005

(54) **ALKALINE LIPASE FROM *VIBRIO METSCHNIKOVII* RH530 N-4-8 AND NUCLEOTIDE SEQUENCE ENCODING THE SAME**

(75) Inventors: Ghee Hong Jin, Seoul (KR); Sung Hoo Jhon, Seoul (KR); Hyun Hwan Lee, Yongin (KR); Hyune Mo Rho, Seoul (KR)

(73) Assignee: CJ Corp. (KR)

( * ) Notice: Subject to any disclaimer, the term of this patent is extended or adjusted under 35 U.S.C. 154(b) by 0 days.

(21) Appl. No.: 10/603,260

(22) Filed: Jun. 24, 2003

(65) Prior Publication Data

US 2004/0009570 A1 Jan. 15, 2004

(30) Foreign Application Priority Data

Jun. 24, 2002 (KR) .................. 10-2002-0035410

(51) Int. Cl.$^7$ ............ C12N 9/20; C12N 1/20; C12N 15/00; C07H 21/04

(52) U.S. Cl. ............... 435/198; 435/252.3; 435/320.1; 536/23.2

(58) Field of Search .............. 435/198, 252.3, 435/320.1; 536/23.2

(56) References Cited

FOREIGN PATENT DOCUMENTS

| KR | 0145277 | 4/1998 |
|---|---|---|
| KR | 1999-0084319 | 12/1999 |

*Primary Examiner*—Tekchand Saidha
(74) *Attorney, Agent, or Firm*—Cantor Colburn LLP

(57) ABSTRACT

An alkaline lipase isolated from *Vibrio metschnikovii* RH530 and a polynucleotide sequence encoding the same are provided. The isolated alkaline lipase has an amino acid sequence of SEQ ID NO: 5 and the polynucleotide having a base sequence of SEQ ID NO: 4 encodes the alkaline lipase. The isolated alkaline lipase exhibits an optimal activity at a high pH level, that is, at pH 10~11, and has very high ratio of residual enzyme activity and high compatibility with a surfactant, so that it can be suitably used as an enzyme for a laundry detergent.

13 Claims, 13 Drawing Sheets

Fig 4A.

| | | | | | | | | | | | | |
|---|---|---|---|---|---|---|---|---|---|---|---|---|
| (SEQ ID NO:1) | 1 | AGC | TTG | CAC | TTT | ATC | AGC | CAA | TAC | TTG | CAT | CGG | TAA |
| | 37 | CTC | GGC | GGG | CAC | TTG | TGC | CCA | GTG | GCG | GCG | GCT | ACG |
| | 73 | TAC | TTC | AGA | GAT | TAA | GGC | CAT | GAC | TAG | CGT | TTC | ATA |
| | 109 | TAA | AAT | GGT | GTC | TCG | CCA | CGT | ACC | TTG | AAT | GGC | GAT |
| | 145 | ACG | CAG | CTG | GCG | TTT | GCC | CTC | TTG | CTT | GAG | GAT | CCC |
| | 181 | GAT | TTC | AAT | TTG | CCG | ATC | GGG | TTG | AAA | ATG | GAA | ATA |
| | 217 | GCG | TAA | TGA | CTG | TAA | AAA | AGT | ACG | ATT | CAA | ATG | AGG |
| | 253 | TGC | ATG | CTG | CTC | TAA | ATA | AAC | AAT | GTC | GGC | ATC | CGA |
| | 289 | AAA | GCG | CAA | TGA | AGC | CAA | CTG | ATT | GAT | TTC | TTG | GCG |
| | 325 | TAC | TTC | CTC | TAA | TAA | ATC | GCT | AAT | GTC | TTC | ATC | ACT |
| | 361 | GCG | CAC | AAT | CAA | TTC | ATA | GCG | CAC | CTC | AAC | ATC | CGG |
| | 397 | ATA | CAA | CGA | ATG | AAC | GGC | CTG | CAT | CAT | ATT | GAT | TTT |
| | 433 | ATA | GGC | ATC | AAG | ATC | CAA | TAA | ACT | GCG | GAT | AAA | AAG |
| | 469 | AGG | AGA | AAA | TAG | GCG | ATC | GCT | CAT | GAT | GAT | GCC | ATC |
| | 505 | CTT | TCG | TTC | GGT | TTC | ATT | CAG | TCA | TTA | CGT | TAG | TAA |
| | 541 | CAA | CGT | GTT | GCT | AAC | TTT | GGG | CGA | ACA | ATA | AAG | TAC |
| | 577 | CCT | TGT | AAG | TTT | GTC | AAC | TTT | TGT | GAC<br>-35 | AAA | CCT | AGT |
| | 613 | CAG | TCG | TTA | TTT | GGC | CTT | ATT | ATA<br>-10 | ATT | ATG | GAT | ATT |
| | 649 | GAG<br>S | GGG<br>D | TAA | GGA | CGT | AGT | CAT | AAC | AAC | AAT | TAC | AGT |
| | 685 | ACT | CTT | GTT | ATC | TGA | GTT | ATG<br>M | TTT<br>F | GTC<br>V | ACA<br>T | AAG<br>K | TCT<br>C |
| (SEQ ID NO:3) | 1 | | | | | | | M | F | V | T | K | C |
| | 721 | TAT | TTA | CAT | TTG | ACC | ATC | ATC | ATG | CAC | TTA | CCT | AAA |
| | 7 | Y | L | H | L | T | I | I | M | H | L | P | K |
| | 757 | ATA | AGC | CCG | TTG | TTT | ATT | AGG | GAA | GCC | ATT | ATG | ATT |
| | 19 | I | S | P | L | F | I | R | E | A | I | M | I |
| | 793 | GTC | ACT | ATC | GAT | ATG | ATT | TGT | CTG | CGT | CTT | GCG | CCG |
| | 31 | V | T | I | D | M | I | C | L | R | L | A | P |
| | 829 | AAA | TCT | ATC | CAG | GTT | TTA | CTG | GTG | AAA | CGC | TCT | AAT |
| | 43 | K | S | I | Q | V | L | L | V | K | R | S | M |
| | 865 | CCA | AAT | CGG | CCA | GAT | TGT | GGT | AAA | TGG | GCA | TTG | CCT |
| | 55 | P | N | R | P | D | C | G | K | W | A | L | P |
| | 901 | GGC | GGG | ATA | GTG | TAT | GAC | GAA | GAT | ATG | ACC | GCT | CAT |
| | 67 | G | G | I | V | Y | D | E | D | M | T | A | H |
| | 937 | GGT | GGA | GAA | CCT | GTC | GAT | GAG | GAT | TTT | GAT | GCA | GCG |
| | 79 | G | G | E | P | V | D | E | D | F | D | A | A |
| | 973 | AGA | CGA | CGT | ATT | TGT | CGG | CAA | AAA | GTC | CAT | ACT | TAT |
| | 91 | R | R | R | I | C | R | Q | K | V | H | T | Y |
| | 1009 | CCT | AAT | TTT | ATC | AGC | GAT | CCG | CTG | GTT | GAT | GGC | AAC |
| | 103 | P | N | F | I | S | D | P | L | V | D | G | N |
| | 1045 | CCC | AAA | CGC | GAT | CCG | AAT | GGT | TGG | AGT | GTC | AGT | ATT |
| | 115 | P | K | R | D | P | N | G | W | S | V | S | I |
| | 1081 | TCC | CAT | TAC | GCT | TTA | TTA | AAC | CCG | TGG | AAT | GTC | AAA |
| | 127 | S | H | Y | A | L | L | N | P | W | N | V | K |
| | 1117 | CAA | ATA | GAA | GAT | TTT | GGT | ATC | GAC | CCC | GAG | CGC | GCT |
| | 139 | Q | I | E | D | F | G | I | D | P | E | R | A |
| | 1153 | AAT | TGG | TTT | GAT | CTT | CAT | ACT | TTA | CTC | AAA | GAA | GAA |
| | 151 | N | W | F | D | L | H | T | L | L | K | E | E |
| | 1189 | ATG | CCG | CTG | GCT | TTT | GAT | CAT | GTC | GCG | CAA | ATT | CAG |
| | 163 | N | P | L | A | F | D | H | V | A | Q | I | Q |
| | 1225 | CAT | GCG | TGG | CAA | AAA | TTA | CGC | GCT | GCG | GTT | GAA | TAC |
| | 175 | H | A | W | Q | K | L | R | A | A | V | E | Y |
| | 1261 | ACA | TCC | GTG | GTA | CTA | TTT | TCA | TTA | GAA | AAA | GAG | TTT |
| | 187 | T | S | V | V | L | F | S | L | E | K | E | F |
| (SEQ ID NO:1) | 1297 | TTA | GTG | GCG | GAT | ATT | ATT | GAT | GCC | TAC | GCC | AAA | TTT |
| (SEQ ID NO:3) | 199 | L | V | A | D | I | I | D | A | Y | A | K | F |

Fig 4B.

```
(SEQ ID NO:1) 1333  GGC  GTC  GAA  GTT  AAT  CGC  ATG  ACC  ATT  AAA  CGC  CGC
               211   G    V    E    V    N    R    M    T    I    K    R    R
              1369  TTG  ATC  AAT  ACC  GGG  GTG  ATC  GTC  AGT  ACC  AAT  AAA
               223   L    I    N    T    G    V    I    V    S    T    N    K
              1405  ATG  GCC  GCA  TCT  TGT  AAA  GGC  AAA  GGA  GCC  AAA  CCA
               235   M    A    A    S    C    K    G    K    G    G    K    P
              1441  GCC  ACC  GTT  TAT  CGT  CTT  GCC  AGT  CAT  GAA  GTC  ACC
               247   A    T    V    Y    R    L    A    S    H    E    V    T
              1477  TAT  TTT  CAA  ACC  TGT  TTA  CGA  GGT  TAA  CTG  TTC  GAA
(SEQ ID NO:3)  259   Y    F    Q    T    C    L    R    G
              1513  AAT  CGT  GTA  CAG  TAG  GTG  ATG  ATG  TCA  ATT  GAT  GAT
              1549  AGG  TAG  GAA  GCA  ATG  CAG  ATT  ATT  CTT  GTT  CAT  GGA
(SEQ ID NO:5)   1                        M    Q    I    I    L    V    H    G
              1585  CTC  TAT  ATG  CAT  GGC  TTG  GTA  ATG  CAT  CCG  CTT  AGT
                9    L    Y    M    H    G    L    V    M    H    P    L    S
              1621  CAT  CGT  CTG  CAT  AAA  TTG  GGT  TAT  CGT  ACT  CAA  ACC
                21   H    R    L    H    K    L    G    Y    R    T    Q    T
              1657  ATT  AGC  TAC  AAC  TCA  CTC  GCT  ATC  GAT  GAT  GAG  GCC
                33   I    S    Y    N    S    L    A    I    D    D    E    A
              1693  ATT  TTT  CGC  CGC  CTT  GAC  CGA  TCG  CTC  ACT  CAT  GCC
                45   I    F    R    R    L    D    R    S    L    T    H    A
              1729  TCG  CCT  AAT  GCT  TTA  GTC  GGA  CAC  AGT  TTG  GGC  GGA
                57   S    P    N    A    L    V    G    H    S    L    G    G
              1765  TTG  GTG  ATC  AAA  CGT  TAT  CTA  GAA  TCG  CGC  GCA  CCG
                69   L    V    I    K    R    Y    L    E    S    R    A    P
              1801  TCC  TGT  GAA  ACC  CTC  TCC  CAT  GTC  GTC  GCC  ATC  GGC
                81   S    C    E    T    L    S    H    V    V    A    I    G
              1837  TCA  CCT  TTG  CAA  GGA  GCT  TCC  ATT  GTC  AAT  AAA  ATT
                93   S    P    L    Q    G    A    S    I    V    N    K    I
              1873  GAG  CAA  TTA  GGT  TTA  GGG  GTG  GCA  CTA  GGT  AAT  TCA
               105   E    Q    L    G    L    G    V    A    L    G    M    S
              1909  GCA  GAA  TTT  GGG  TTA  AAA  GAA  CAC  GAC  GAC  GAA  TCC
               141   A    E    F    G    L    K    E    H    D    D    E    W
              1945  CGC  TAT  CCA  CAA  AAA  TCA  GGC  AGT  ATT  GCA  GGA  ACG
               177   R    V    P    Q    K    L    G    S    I    A    G    T
              1981  ATA  CCT  TTA  GGG  CTG  CGC  AGC  CTT  TTA  CTG  CGC  GAT
               213   I    P    L    G    L    R    S    L    L    L    R    D
              2017  CCA  CTG  GAC  TCC  GAT  GGT  ACC  GTC  ACA  GTA  GAA  GAA
               225   Q    L    D    S    D    G    T    V    T    V    E    E
              2053  ACC  AAA  ATA  GCT  GGC  ATG  ACA  GAT  CAT  ATC  GCG  ATA
               237   T    K    I    A    G    M    T    D    H    I    A    I
              2089  TCC  ACC  ACT  TCA  TAC  GAG  AAT  GCT  GTT  TAA  TCA  TTC
(SEQ ID NO:5)  249   S    T    T    S    Y    E    N    A    V
              2125  CGT  TGC  CGA  GCA  AAT  CGA  CCA  CTT  TCT  TCG  TTA  TGA

2161  CCG  CTT  CCG  GCG  CTA  AAG  CCG  TTT  AAA  CTT  CAG  ATG
              2197  ATA  GTG  TAC  TTC  GTA  TCA  AAC  CGA  TGG  TGA  TTG  AAA
              2233  ACA  TAC  CCA  CCA  TTC  ATT  CAG  AAT  AAG  ACG  TTG  CCA
              2269  TCA  TCA  GAG  CTT  TCC  CAT  GCA  ATA  AAC  AAT  CCG  CGA
              2305  CTT  TAC  GTC  TGG  CCG  CTT  TAA  CTA  AAT  TGG  CAA  GTG
              2341  TCT  GCC  GCG  ATA  CGC  TGA  TGC  CGC  ATA  GTT  AAG  CCA
              2377  GCC  CCG  ACA  CCC  GCC  AAC  ACC  CGC  TGA  CGC  GCC  CTG
              2413  ACG  GGC  TTG  TCT  GCT  CCC  GGC  ATC  CGC  TTA  CAG  ACA
              2449  AGC  TGT  GAC  CGT  CTC  CGG  GAG  CTG  CAT  GTG  TCA  GAG
              2485  GTT  TTC  ACC  GTC  ATC  ACC  GAA  ACG  CGC  GAG  ACG  AAA
              2521  GGG  CCT  CGT  GAT  ACG  CCT  ATT  TTT  ATA  GGT  TAA  TGT
(SEQ ID NO:1) 2557  CAT  GAT  AAT  AAT  GGT  TTC  TTA  G
```

Fig 6.

| | |
|---|---|
| *Vibrio metschnikovii* | M Q I I L V H G L Y M H G L V M H P L S H R L H K L G Y R T (SEQ ID NO:5;1-30) |
| *Pseudomonas glumae* | V A N L S G F (SEQ ID NO:6;1-7) |
| *Burkholderia cepacia* | V A N L S G F (SEQ ID NO:7;1-7) |
| *Vibrio metschnikovii* | Q T I S Y N S L A I D D E A I F R R L D R S L T H A S P N A (SEQ ID NO:5;31-60) |
| *Pseudomonas glumae* | Q S D D G P N G R G E Q L L A Y V K Q V L A T T G A T K V N (SEQ ID NO:6;8-37) |
| *Burkholderia cepacia* | Q S D D G P N G R G E Q L L A Y V K T V L A T T G A T K V N (SEQ ID NO:7;8-37) |
| *Vibrio metschnikovii* | L V |G H S L G| G L V I K R Y L E S R A F S C E T L S H V V A (SEQ ID NO:5;61-90) |
| *Pseudomonas glumae* | L I |G H S Q G| G L T - S R Y V A A V A P - - Q L V A S V T T (SEQ ID NO:6;38-64) |
| *Burkholderia cepacia* | L V |G H S Q G| G L S - S R Y V A A V A P - - D L V A S V T T (SEQ ID NO:7;38-64) |
| *Vibrio metschnikovii* | I G S P L Q G A S I V N K I E Q L G L G V A L G N S A E F G (SEQ ID NO:5;91-120) |
| *Pseudomonas glumae* | I G T R H R G S E F A D F V Q D V L K T D P T G L S S T V I (SEQ ID NO:6;65-94) |
| *Burkholderia cepacia* | I G T R H R G S E F A D F V Q D V L A Y D P T G L S S S V I (SEQ ID NO:7;65-94) |
| *Vibrio metschnikovii* | L K E H D D E W R Y P Q K L G S I A G T I P L G L R S L L L (SEQ ID NO:5;121-150) |
| *Pseudomonas glumae* | A A F V N V F G T L V S S S H N T D Q D A L A (SEQ ID NO:6;95-117) |
| *Burkholderia cepacia* | A A F V N V F G I L T S S S H N T N Q D A L A (SEQ ID NO:7;95-117) |
| *Vibrio metschnikovii* | R D Q L D S D G T V T V E E T K I A G M T D H I A I S T T S (SEQ ID NO:5;151-180) |
| *Pseudomonas glumae* | |
| *Burkholderia cepacia* | |
| *Vibrio metschnikovii* | Y E N A V (SEQ ID NO:5;181-185) |
| *Pseudomonas glumae* | |
| *Burkholderia cepacia* | |

ALKALINE LIPASE FROM *VIBRIO METSCHNIKOVII* RH530 N-4-8 AND NUCLEOTIDE SEQUENCE ENCODING THE SAME

BACKGROUND OF THE INVENTION

This application claims priority from Korean Patent Application No. 2002-35410, filed on Jun. 24, 2002, in the Korean Intellectual Property Office, the disclosure of which is incorporated herein in its entirety by reference.

1. Field of the Invention

The present invention relates to an alkaline lipase isolated from *Vibrio metschnikovii* RH530 N-4–8 and a gene encoding the same. The present invention also relates to a recombinant vector containing the gene, a transformed host cell transformed with the recombinant vector and a method of producing an alkaline lipase using the transformed host cell.

2. Description of the Related Art

An alkaline lipase hydrolyses triacylglycerol into glycerol and fatty acid at alkaline pH. Various microorganisms producing an alkaline lipase have been reported. Specifically, representative examples of such microorganisms include *Pseudomonas,* and *Bacillus.* These enzymes have been applied to industrial fields of detergents that necessitate hydrolysis of lipids under alkaline conditions.

Currently, lipases for commercially available detergents biochemically exhibit an optimal activity at weak alkaline pH, that is, at pH 8~9, and are relatively rapidly inactivated in the presence of an anionic surfactant, e.g., LAS.

Thus, there is demand for lipases exhibiting an optimal activity at a higher pH level, e.g., at pH 10~11, a high ratio of residual enzyme activity and high compatibility with surfactants.

In order to overcome problems with prior art, inventors of the present invention found out that *Vibrio metschnikovii* RH530 N-4–8 (on deposit at the Korean Collection for Type Culture (KCTC) with KFCC-11030 on Feb. 23, 1998), which is a strain producing protease for a detergent, as disclosed in Korean Patent laid-open Nos. 10-1996-0007772 and 10-1999-0084319, also produced a lipase. They intensively studied biochemical properties of the lipase, a gene encoding the lipase and its resistance to a surfactant and completed the present invention.

SUMMARY OF THE INVENTION

The present invention provides a lipase exhibiting an optimal activity at a high pH level, that is, at pH 10~11, and having a high residual enzyme activity and high compatibility with a surfactant.

According to an aspect of the present invention, there is provided gene encoding the lipase.

According to another aspect of the present invention, there is provided recombinant vector containing the gene encoding the lipase.

According to another aspect of the present invention, there is provided transformed host cell transformed by the recombinant vector.

According to another aspect of the present invention, there is provided a method of producing the lipase by cultivation of the host cell.

BRIEF DESCRIPTION OF THE DRAWINGS

The above and other features and advantages of the present invention will become more apparent by describing in detail exemplary embodiments thereof with reference to the attached drawings in which:

FIGS. 4A and 4B show a base sequence of a DNA insert containing the alkaline lipase gene from *Vibrio metschnikovii* RH530 N-4–8 according to the present invention, a regulatory element and an amino acid sequence derived therefrom;

FIG. 6 shows the comparison result of an amino acid sequence deduced from the alkaline lipase gene according to the present invention with *Pseudomonas glumae,* and *Burkholderia cepacia;*

DETAILED DESCRIPTION OF THE INVENTION

Figure 1:
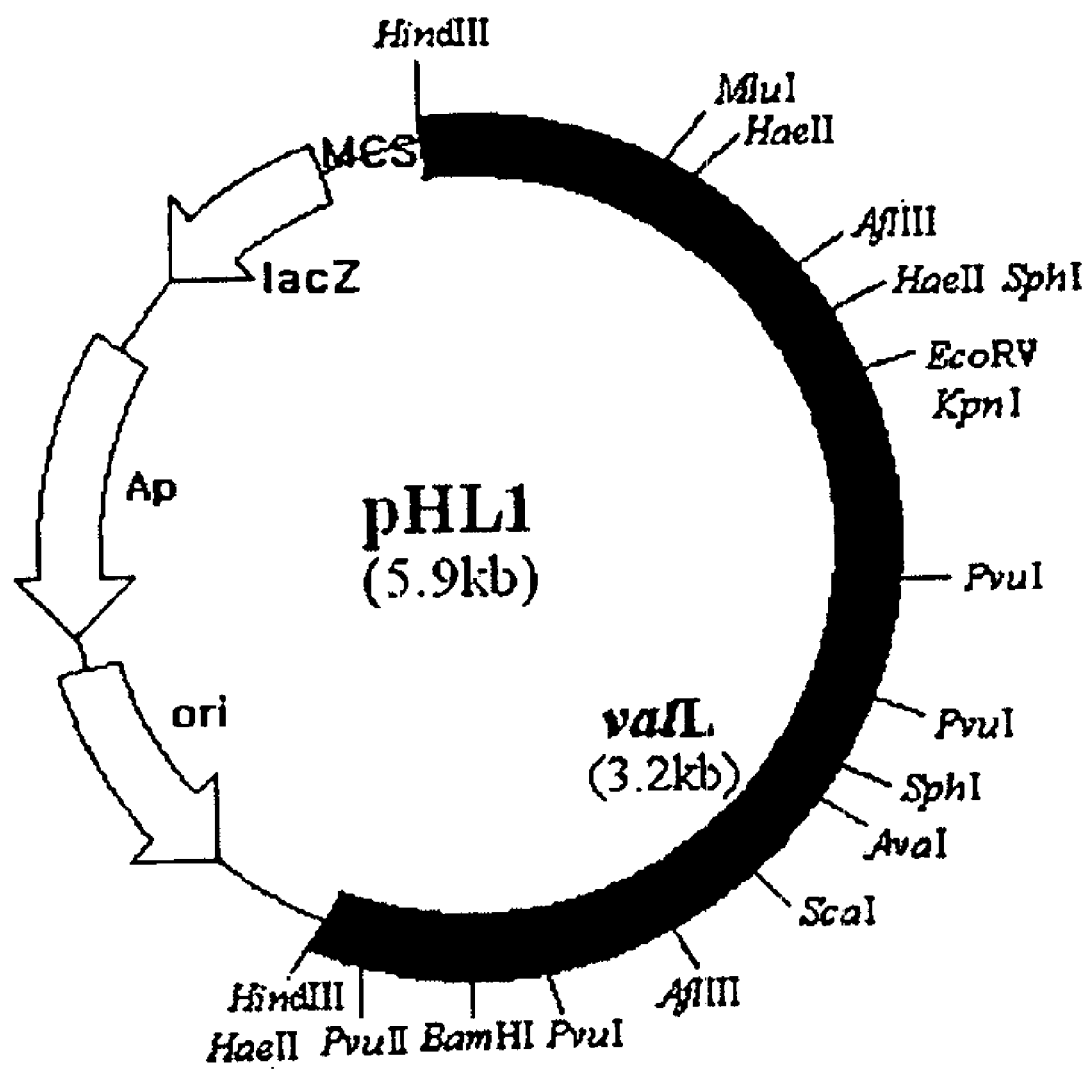
FIG. 1 shows a recombinant vector pHL1 containing 3.2 kb DNA insert (valL) having an alkaline lipase gene according to the present invention.

An alkaline lipase from *Vibrio metschnikovii* RH530 N-4–8 according to the present invention has an amino acid sequence of SEQ ID NO: 5.

Also, a polynucleotide according to the present invention encodes an amino acid sequence of SEQ ID NO: 5. The polynucleotide includes polynucleotide containing a nucleotide sequence of SEQ ID NO: 4, polynucleotide containing a nucleotide sequence of SEQ ID NO: 2 and a nucleotide sequence of SEQ ID NO: 4, for example. Also, the polynucleotide may have a nucleotide sequence of SEQ ID NO: 1.

A recombinant vector according to the present invention includes a polynucleotide encoding an amino acid sequence of SEQ ID NO: 5, preferably a polynucleotide having a nucleotide sequence of SEQ ID NO: 4. Preferably, the recombinant vector is pHL1, pHLB29 or pHAAH38.

A transformed host cell according to the present invention is transformed by the recombinant vector including a polynucleotide encoding an amino acid sequence of SEQ ID NO: 5, preferably a polynucleotide having a nucleotide sequence of SEQ ID NO: 4. The recombinant vector is preferably pHL1, pHLB29 or pHMH38. Preferably, the transformed host cell is *E. coli* transformed by the recombinant vector. The transformed *E. coli* is preferably HB101 harboring pHL1.

A method of producing the alkaline lipase from *Vibrio metschnikovii* RH530 N-4–8 according to the present invention includes culturing the transformed host cell.

Also, a detergent according to the present invention includes an alkaline lipase from *Vibrio metschnikovii* RH530 N-4–8 having an amino acid sequence of SEQ ID NO: 5. The detergent is preferably in a liquid or particulate form.

The present invention will now be described in more detail with reference to various embodiments. These embodiments are provided for illustration only and the invention is not limited to the specific embodiments.

EXAMPLES

The examples of the present invention are based on the finding that *Vibrio metschnikovii* RH530 N-4–8, which is known as a strain producing protease for a detergent, as disclosed in Korean Patent laid-open Nos. 10-1996-0007772 and 10-1999-0084319, produces a lipase. Biochemical properties of the lipase, a gene encoding the lipase and its resistance to a surfactant have been intensively studied.

In order to isolate a gene encoding an alkaline lipase, *Vibrio metschnikovii* RH530 N4–8 was cultured to collect a cell. The cell was lysed with lysozyme treatment. The resultant product was treated with phenol and chloroform to remove protein and was subjected to centrifugation to remove precipitate, giving a supernatant. *Vibrio* chromosomal DNA was obtained from the supernatant. The obtained chromosomal DNA was cut with a restriction enzyme and inserted into a cloning vector pUC19, producing recombinant vectors including pHL1, pHLB29 and so on, which was transformed into *E. coli*. Screening for right clones was performed with LB media containing 0.5~1% tributyrin or tricaprylin as a lipase substrate, 0.1% polyoxyethylene (7EO) as an emulsifier. 1.8% agarose were added to produce a medium shown in Table 1 and a strain forming a clear halo around a colony grown in the medium was selected. The thus selected recombinant *E. coli* was referred to as HB101(pHL1).

The activity of a lipase was measured using a crude enzyme solution extracted from the recombinant *E. coli* HB101(pHL1) at a weak alkaline pH, confirming expression of an alkaline lipase.

The recombinant vector was cut with a restriction enzyme and a base sequence of heterogenous DNA fragment inserted into the recombinant vector.

Example 1
Cloning of Alkaline Lipase Gene

Figure 2:
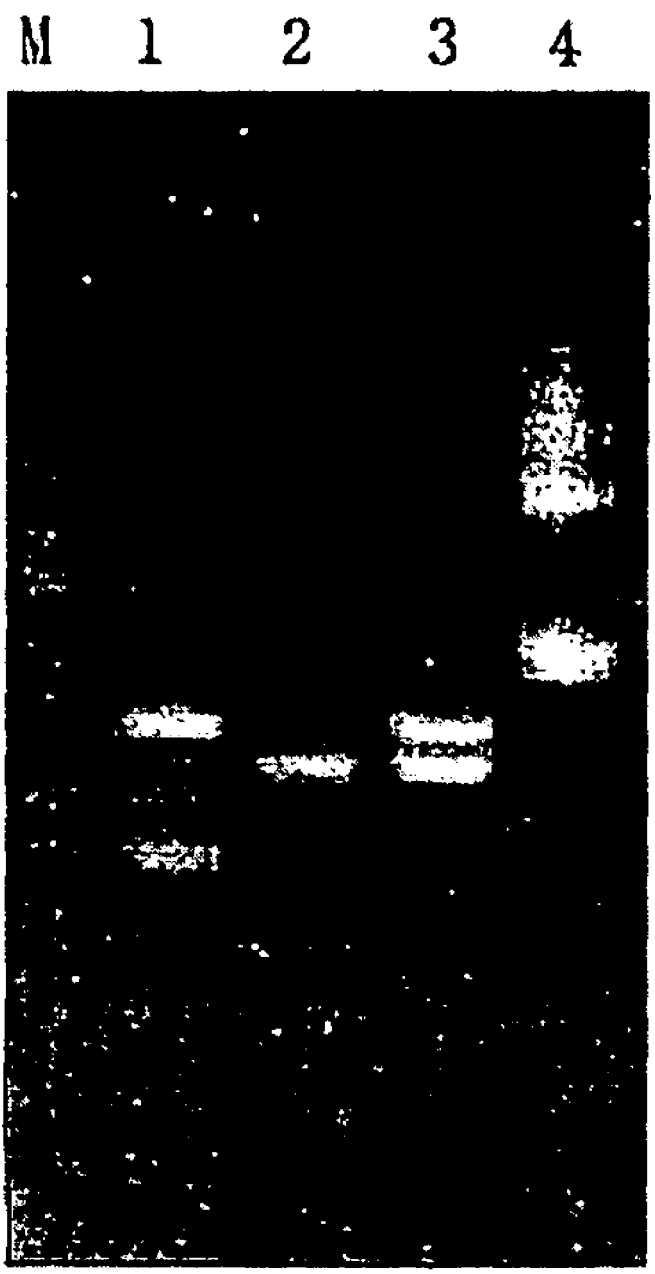
FIG. 2 shows an agarose gel electrophoresis of the recombinant vector pHL1 having an alkaline lipase gene according to the present invention, in which M denotes a size marker, lane 1 has a supercoiled type pUC19, lane 2 has a pUC19 digested with HindIII, lane 3 has a recombinant vector pHL1 digested with HindIII, the band of 2.7 kb corresponding to a vector pUC19 and the band of 3.2 kb corresponding to a DNA insert containing the alkaline lipase gene according to the present invention, and lane 4 has a supercoiled type recombinant vector pHL1.

*Vibrio metschnikovii* RH530 N-4–8 was cultured at 30° C. using the culture medium shown in Table 1 to collect a cell and treated with lysozyme to lyse the cell. The resultant product was treated with phenol and chloroform to remove protein, and a precipitate was removed by centrifugation, giving a supernatant. A Vibrio chromosomal DNA was obtained from the supernatant. The obtained chromosomal DNA was cut with a restriction enzyme HindIII to be recombined with cloning vector pUC19, followed by transforming *E. coli* HB101, thereby cloning a DNA fragment containing a 3.2 kb alkaline lipase gene. The resulting recombinant vector was referred to as a vector pHL1 (FIG. 1). After treatment with the restriction enzyme HindIII, an electrophoresis with 1% agarose gel was performed. The agarose gel electrophoresis showed that the alkaline lipase gene was cloned (FIG. 2).

TABLE 1

| LSC Medium | |
|---|---|
| Composition | Content (g/L) |
| Trypton | 10 |
| Yeast extract | 5 |
| Sodium chloride | 10 |
| 1 M Sodium carbonate buffer, pH 10.5 | 100 (ml/L) |

Example 2
Southern Blotting of pHL1

In order to confirm that a DNA fragment containing an alkaline lipase gene derived from *Vibrio metschnikovii*, which is contained in a recombinant vector pHL1 shown in FIG. 1, is identical with the gene from *Vibrio metschnikovii*, Southern blotting was performed.

Figure 3A:
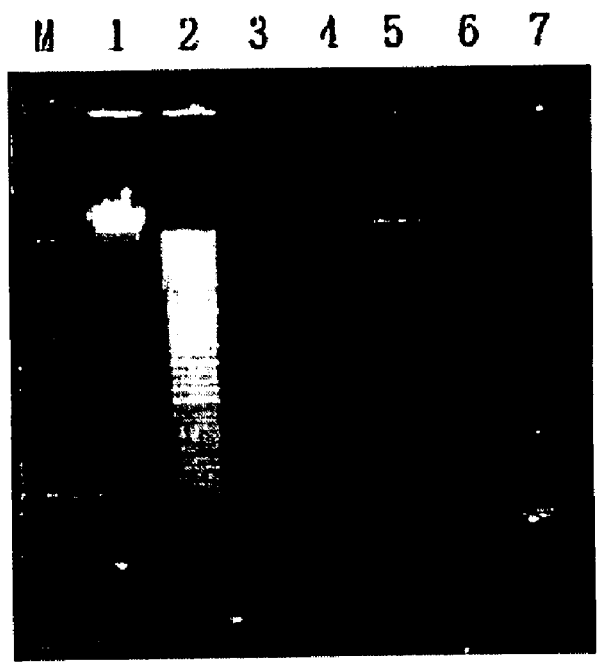
FIG. 3A shows an agarose gel electrophoresis of a DNA fragment containing the alkaline lipase gene according to the present invention.
Figure 3B:
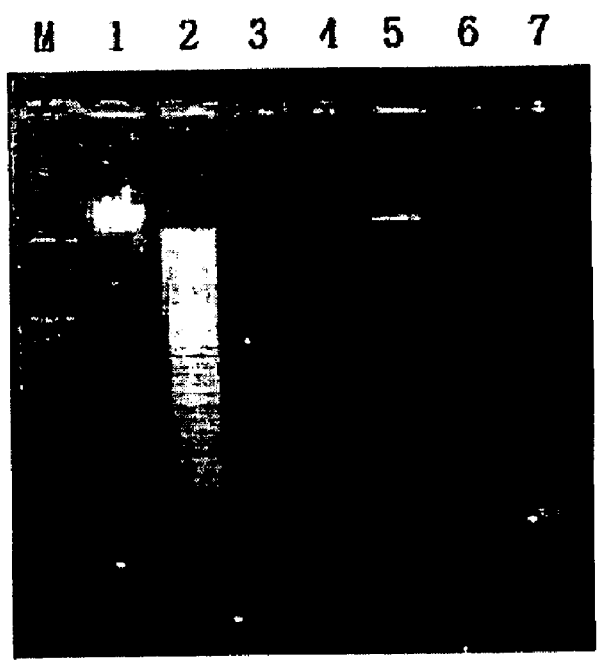
FIG. 3B shows a photograph of Southern blotting, in which M denotes a size marker marked by DIG, lane 1 has *Vibrio metschnikovii* chromosomal DNA, lane 2 has *Vibrio metschnikovii* chromosomal DNA digested with HindIII, lane 3 has *Vibrio metschnikovii* chromosomal DNA digested with AvaI and EcoRI, lane 4 has pUC19 digested with HindIII, lane 5 has a supercoiled type recombinant vector pHL1, lane 6 has a recombinant vector pHL1 digested with HindIII, and lane 7 has recombinant vector pHL1/AvaI and EcoRI (probe)

A 0.8 kb DNA fragment labeled with DIG (DIG DNA Labelling Kit, Roche Diagnostics), which was obtained by cutting pHL1 using restriction enzymes Ava I and EcoR I, was used as a probe, and blotted with a chromosomal DNA extracted from the original strain, that is, *Vibrio metschnikovii* RH530 N-4–8, resulting in a colored band at 3.2 kb, as shown in FIGS. 3A and 3B.

It was confirmed that a gene contained in the recombinant vector pHL1 was derived from RH530 N-4–8 (FIGS. 3A, 3B and 4)

Example 3
Subcloning for Verifying Position of Lipase Gene

In order to verify an exact position of a gene in the DNA inserted into a recombinant vector, 3.2 kb DNA was treated with an exonuclease Bal31 to subclone the same in a minimum length required for expression of a lipase.

Production of the lipase was confirmed by formation of a clear halo, and the result of subcloning showed that 2.6 kb DNA fragment was necessary for lipase activity. The recombinant vector containing such a gene having a minimum length was referred to as pHLB29.

2.6 kb DNA fragment was subcloned in a direction opposite to that of a Sma I site of pUC19, and referred to as pHAAH38.

Figure 5:
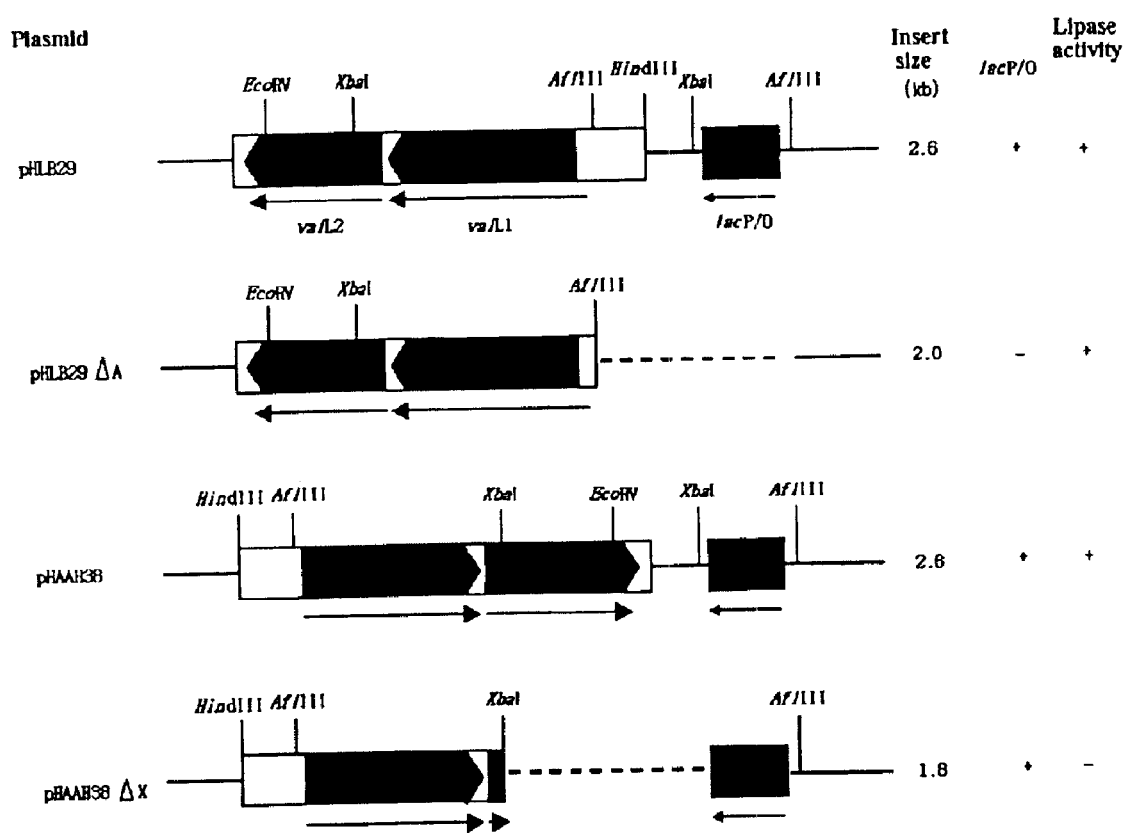
FIG. 5 shows a restriction enzyme map from which a minimum length and a gene position for expression of the alkaline lipase according to the present invention are identified in the DNA insert of the recombinant vector pHL1.

Although the 2.6 kb DNA fragment was subcloned in a reverse direction relative to a lac promoter, pHAAH38 produces a clear halo at a tricaprylin culture medium, confirming that an alkaline lipase promoter exists in the 2.6 kb DNA fragment and the promoter is used when it is transcribed from *E. coli* (FIG. 5).

Example 4
Production of Recombinant Vector for Base Sequence Analysis

A DNA insert of the recombinant vector pHL1 produced above was cut into smaller sizes using various restriction enzymes, and recombined again with pUC19 for transformation of E. coli. A base sequence analysis of the DNA insert in the recombinant vector showed that the base sequence of SEQ ID NO:1 was identified, and two genes ORF1 and ORF2 respectively consisting of 797 bp (SEQ ID NO:2) and 554 bp (SEQ ID NO:4) existed under single promoter. Enzymes expressed from the genes were referred to as Val L1 and Val L2, and genes encoding the same were referred to as valL1 and valL2, respectively. The valL1 and valL2 genes have base sequences of SEQ ID NOS: 2 and 4, and the polypeptide encoded by the genes have amino acid sequences of SEQ ID NOS: 3 and 5. It was also found that they had base sequences corresponding to sites −35 and −10 and a Shine-Dalgarno sequence (SD sequence) (FIG. 4), which are commonly found in a prokaryotic gene. Sequences of these sites and other lipase sequences were compared in view of homology, and the comparison result showed that the second gene was homologous with *Pseudomonas glumae* and *Burkholderia cepacia* lipase genes by 17.5% and 18.3%, respectively. Also, as shown in FIG. 6, the gene had a region corresponding to an active site of a lipase, that is, G-X1-S-X2-G. Thus, it is considered that the gene is a lipase gene, and the first gene is lipase chaperon or an auxiliary gene for extracellular secretion.

Example 5
Measurement of Activity and Stability of Alkaline Lipase

The activity of enzyme was measured using a synthetic substrate p-nitrophenyl palmitate (pNPP), rather than using emulsified natural oil. First, 20 μl of a crude enzyme solution obtained by culturing mother stain, *Vibrio metschnikovii* RH530 or a recombinant strain containing lipase gene, was added to a 880 μl of a buffer solution containing 50 mM tris-HCl (pH 6.8) and 0.5% Arabic gum. Then, 100 μl of a 100 mM p-NPP solution was added to the resultant solution and reacted at 37° C. for 10 minutes. After 10 minutes, 0.5 ml of 3M HCl was added to stop the reaction, followed by centrifuging, adding 3 ml of 2M NaOH to 1 ml of a supernatant. Then, absorbance was measured at 420 nm.

In an alternative method, p-nitrophenyl butyrate (p-NPB) was used as a substrate. First, p-MPB was dissolved in dimethylsulfoxide to prepare a 10 mM substrate solution. 30 μl of the substrate solution was mixed with a buffer solution containing 50 mM tris-HCl and 0.1% triton-X-100 (pH 8.2), 30 μl of a crude lipase solution was added thereto, giving 3 ml of a final product. The final product was also reacted at 37° C. for 10 minutes, and then 3 ml acetone was added to stop the reaction. Then, the absorbance was measured at 405 nm.

Quantitative analysis of protein was based on bovine serum albumin (BSA) using a Lowry's method.

Example 6
Study of Effect of a Region Prior to the Promoter on Enzyme Expression In order to investigate effects of a region prior to the promoter on expression of *Vibrio metschnikovii* alkaline lipase, the region prior to the promoter was removed using restriction enzymes. For measuring enzyme activity, p-nitrophenyl butyrate (p-NPB) was used as a substrate and BamHI and AflIII were used as restriction enzymes. As a result, it was confirmed that removal of 500 bp of the region prior to the promoter resulted in a reduction in enzyme titer by approximately 40%.

Figure 7A:
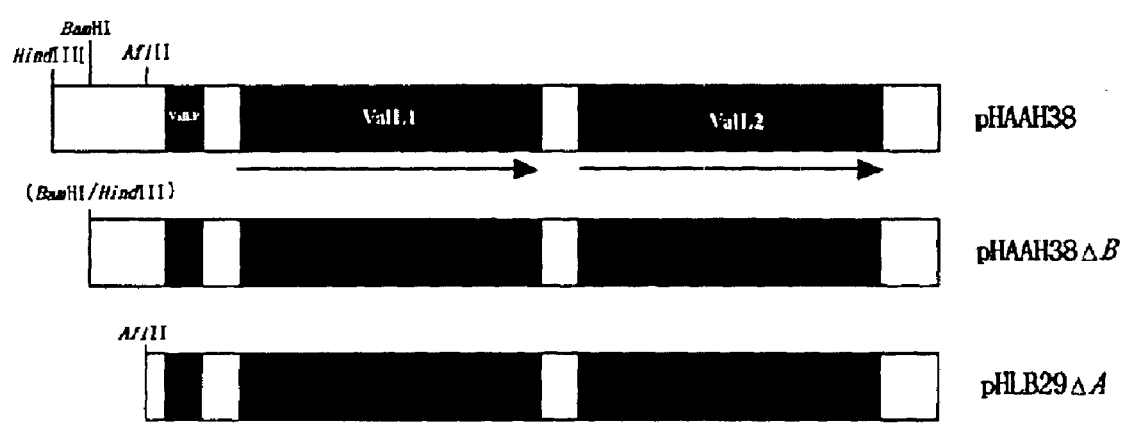
FIG. 7A shows a restriction enzyme map of a region prior to the promoter of the alkaline lipase gene according to the present invention.
Figure 7B:
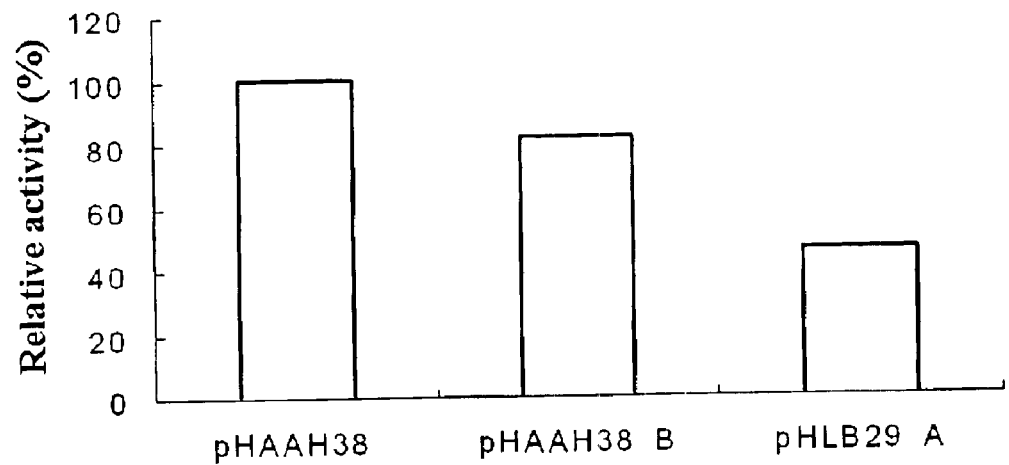
FIG. 7B shows a change in activity when the region prior to the promoter is removed using the restriction enzyme.

Therefore, it could be inferred that expression of an enzyme was greatly influenced by the region prior to the promoter (FIGS. 7A and 7B).

Example 7
Biochemical Properties of Lipase Extracted from Recombinant Strain In order to investigate effects of temperature, pH, surfactant or detergent on the lipase activity, the following experiments were carried out on crude enzyme solutions prepared from recombinant strains containing lipase genes.

(1) Effect of Temperature on Activity and Stability

Figure 8A:
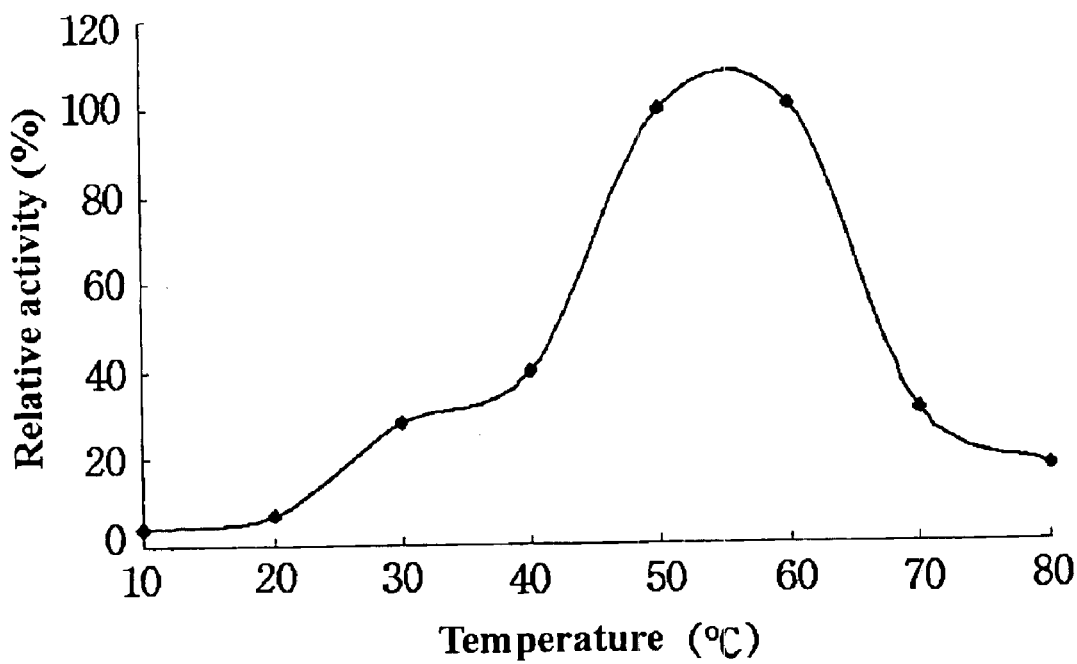
FIG. 8A shows a change in activity of the alkaline lipase according to the present invention.
Figure 8B:
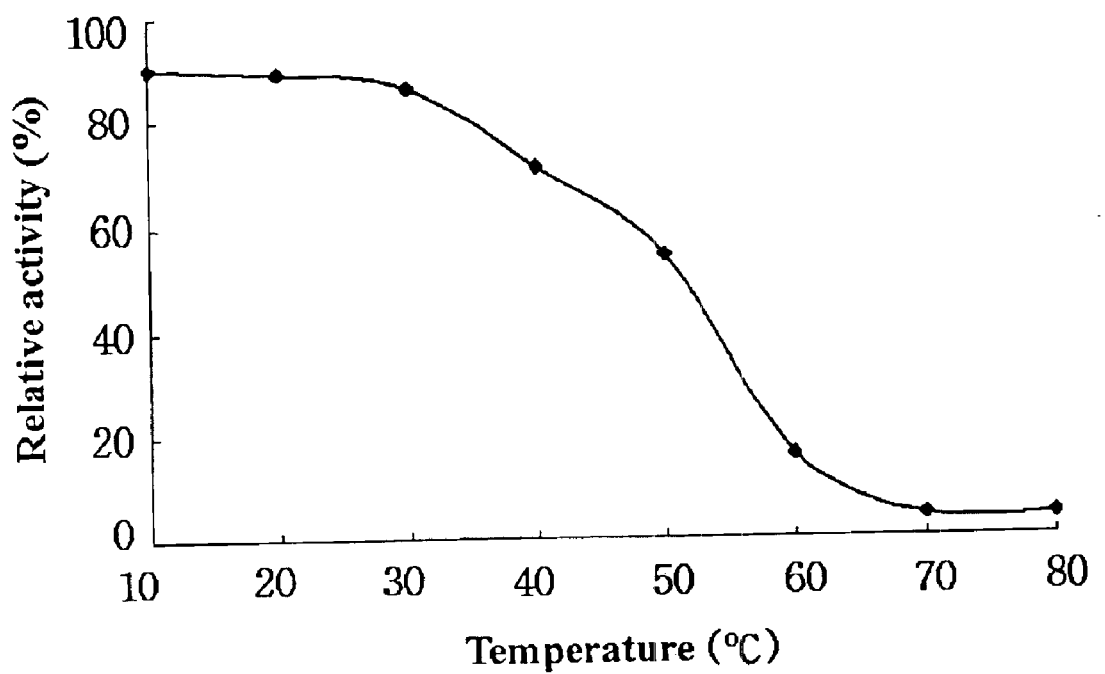
FIG. 8B shows the measuring result of residual activity of the alkaline lipase according to the present invention depending on temperature.

In order to investigate effects of temperature on the activity and stability of an enzyme, *E. Coli* HB101 harboring pHL1 containing a lipase gene was cultured in a culture medium shown in Table 1 for 18 hours to collect a cell. Then, the collected cells were washed twice using saline, and pulverized using a sonicator or French press, followed by centrifuging at 15,000 rpm for 30 minutes, giving a supernatant. The obtained supernatant was used as a crude enzyme solution. The crude enzyme solution was mixed with p-NPB and reacted over various temperature ranges from 10° C. to 80° C. for 2 hours. Then, the activity and stability of the lipase were measured by the above-described titer measuring technique. The measurement result showed that the lipase exhibited highest activity at 50~60° C. Also, the result of residual activity testing showed that the stability increased up to 40° C. and then rapidly decreased from 60° C. (FIGS. 8A and 8B).

(2) Effect of of pH on the Activity and Stability

Figure 9A:
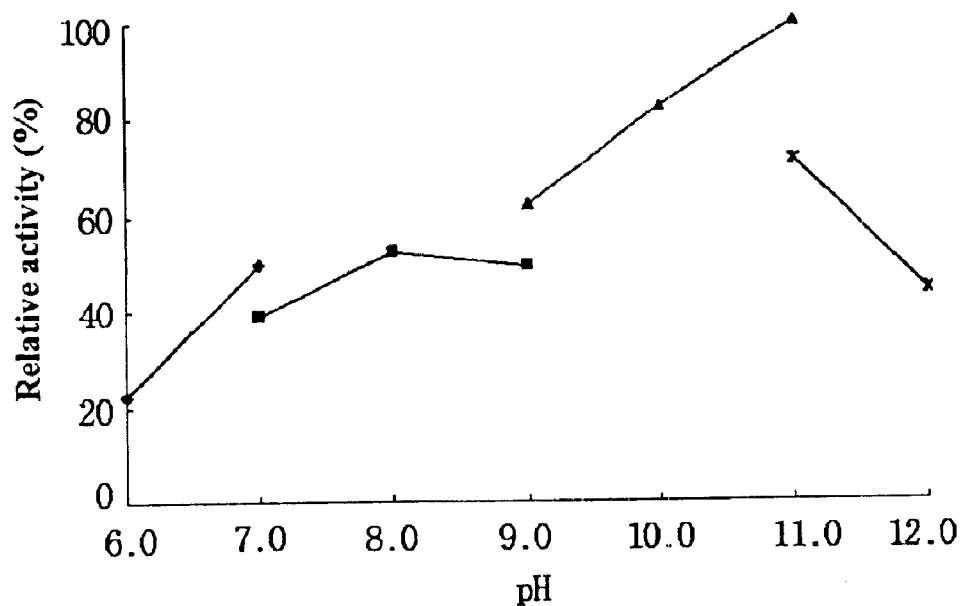
FIG. 9A shows a change in activity of the alkaline lipase according to the present invention depending on pH.
Figure 9B:
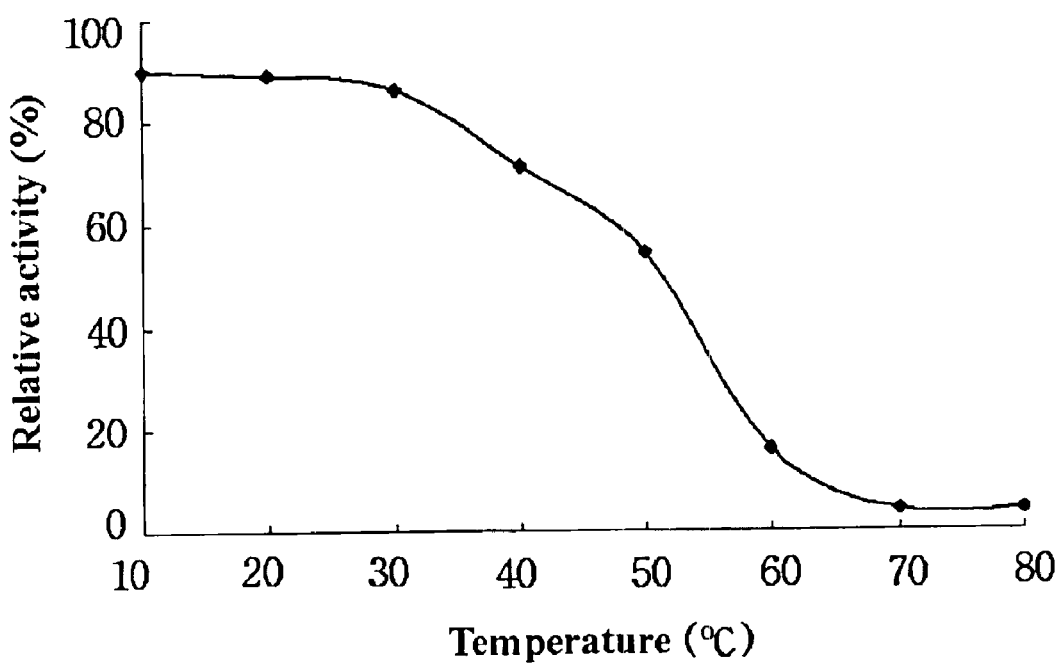
FIG. 9B shows the measuring result of residual activity of the alkaline lipase according to the present invention depending on pH.
Figure 10A:
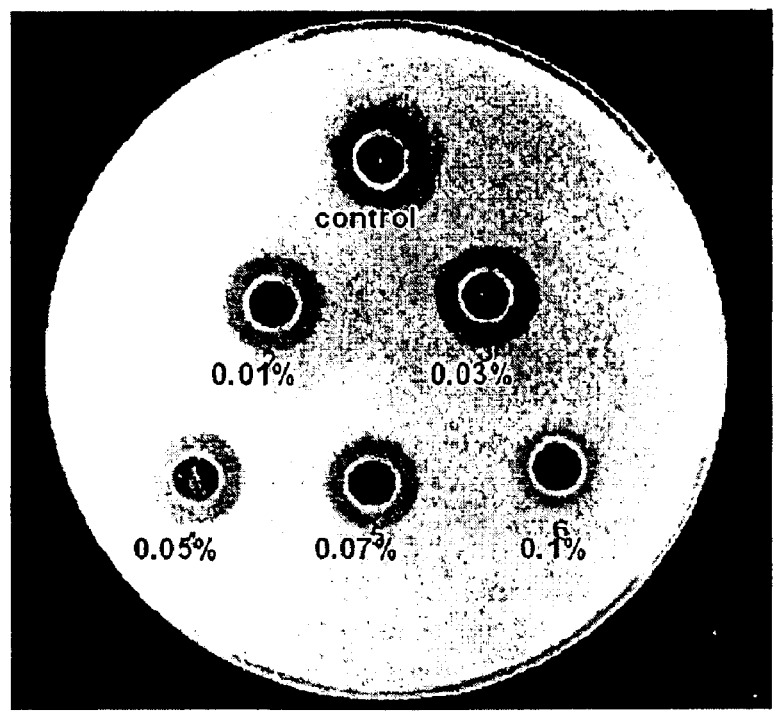
FIG. 10 shows the effect of surfactant or detergent on the activity and stability of the alkaline lipase according to the present invention, for which enzyme solutions mixed with sodium-olefinsulfonate (AOS) (FIG. 10A), sodium alkylbenzen-sulfonate (LAS)(FIG. 10B) and sodium dodecyl sulfate (SDS)(FIG. 10C) are spotted on a 0.5% tricaprylin medium.
Figure 10B:
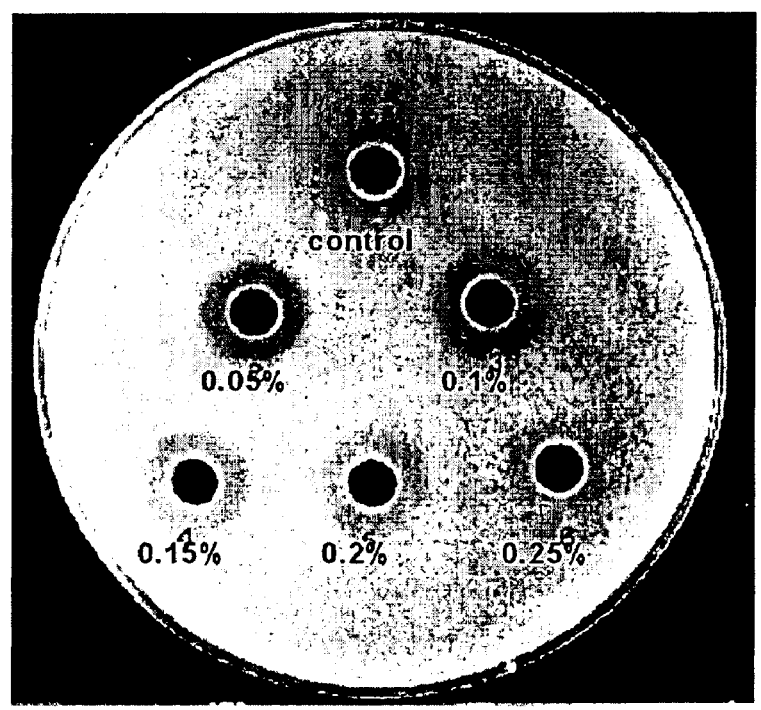
Figure 10C:
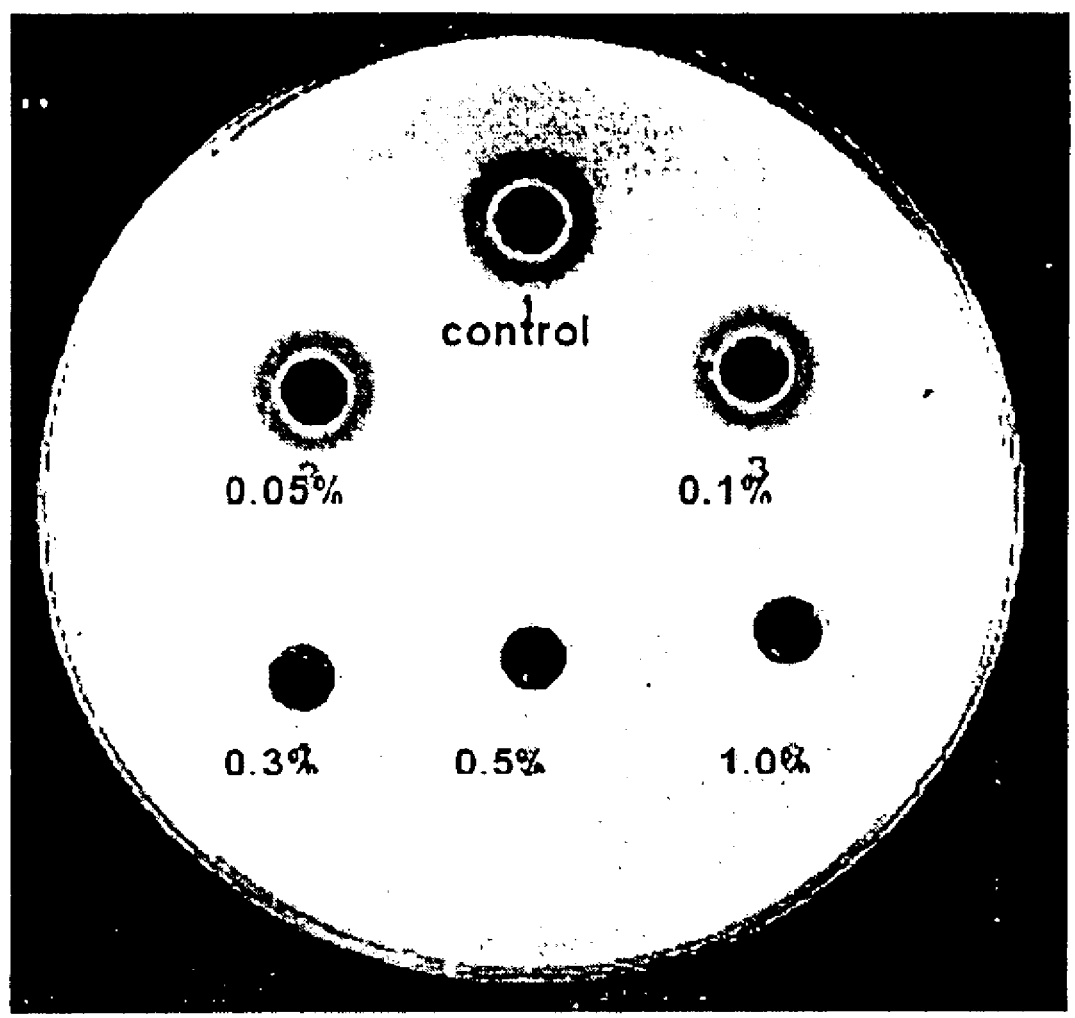

In order to investigate effects of a pH level on the activity and stability of an enzyme, the ratio of residual enzyme activity of the crude enzyme solution extracted in the above-described manner was examined under the same reaction conditions at optimal pH levels in various buffers, including 50 mM sodium phosphate (pH 6~7), as indicated by ♦, 50 mM Tris-HCl (pH 7~9): as indicated by ■, 50 mM sodium carbonate (pH 9~11), as indicated by ▲, and 50 mM sodium phosphate-NaOH (pH 11~12), as indicated by *. The result showed that the optimal pH was 10~11. To examine the residual enzyme activity ratio relative to pH level, each crude enzyme solution was allowed to stand at 20° C. for 12 hours, and then the residual activity was measured. The result showed that the enzyme was very stable at pH in the range of 8~10(FIG. 9B).

(3) Effect of Surfactant on Activity and Stability

In order to measure resistance against a surfactant, which is a main component of a detergent, sodium-alphaolefinsulfonate (AOS), sodium alkylbenzen-sulfonate (LAS), sodium dodecyl sulfate (SDS) were mixed with the crude enzyme solution, followed by spotting the mixture on a 0.5% tricaprylin culture medium.

The result showed that the Vibrio alkaline lipase had resistance against 0.07% LAS and 0.1% AOS.

Also, the *Vibrio* alkaline lipase was active in 0.1% SDS, confirming that the lipase can be suitably used as an additive for a laundry detergent (FIG. 11).

Biochemical properties of general lipases for detergents currently commercially available in the market will now be described. That is, the lipases exhibit an optimal activity at pH 8~9, that is, a weak alkaline level, and are relatively rapidly inactivated in the presence of an anionic surfactant such as LAS. On the other hand, the lipases according to the present invention exhibit an optimal activity at pH 10~11 and had very high ratio of residual enzyme activity and high compatibility with a surfactant. Thus, the lipase according to the present invention is considered to be better than the conventional lipase in view of performance and can be suitably used as an enzyme for a laundry detergent.

Deposit of Recombinant Vectors Produced in the Examples of the Present Invention The recombinant vectors pHL1 and pHLB29 produced in the present invention were on deposit at the Korean Culture Collection Center (KCCM) with KCCM-10384 and KCCM-10385 on Jun. 4, 2002.

INDUSTRIAL APPLICABILITY

According to the present invention, the alkaline lipase has an optimal activity at high pH level, that is, at pH 10~11, a very high ratio of residual enzyme activity and high compatibility with a surfactant, so that it can be suitably used as an enzyme for a laundry detergent.

The gene according to the present invention encodes an alkaline lipase having low homology with other conventional alkaline lipases, an optimal activity at high pH level, that is, at pH 10~11, a very high ratio of residual enzyme activity and high compatibility with a surfactant, the alkaline lipase being suitably used as an enzyme for a laundry detergent.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An isolated alkaline lipase having an amino acid sequence of SEQ ID NO: 5.

2. A isolated polynucleotide comprising a sequence encoding an amino acid sequence of SEQ ID NO: 5.

3. The polyucleotide of claim 2, comprising a nucleotide sequence of SEQ ID NO: 4.

4. The polyucleotide of claim 2, comprising nucleotide sequences of SEQ ID NO: 2 and SEQ ID NO: 4.

5. The polyucleotide of claim 2, comprising a nucleotide sequence of SEQ ID NO: 1.

6. A recombinant vector comprising the polynucleotide of claim 2.

7. The recombinant vector of claim 6, wherein the recombinant vector is pHL1, pHLB29 or pHAAH38.

8. A transformed host cell comprising the recombinant vector of claim 6.

9. The transformed host cell of claim 8, wherein the transformed host cell is *Escherichia coli*.

10. The transformed host cell of claim 9, wherein the transformed host cell is HB101 (pHL1).

11. A method of producing an alkaline lipase comprising culturing the transformed host cell of claim 8.

12. A detergent composition comprising the alkaline lipase of claim 1.

13. The transformed host cell of claim 8, wherein the recombinant vector is pHL1, pHLB29 or pHAAH38.

* * * * *

SEQUENCE LISTING

<160> NUMBER OF SEQ ID NOS: 5

<210> SEQ ID NO 1
<211> LENGTH: 2578
<212> TYPE: DNA
<213> ORGANISM: Vibrio metschnikovii RH530

<400> SEQUENCE: 1

```
agcttgcact ttatcagcca atacttgcat cggtaactcg gcgggcactt gtgcccagtg      60
gcggcggcta cgtacttcag agattaaggc catgactagc gtttcatata aaatggtgtc     120
tcgccacgta ccttgaatgg cgatacgcag ctggcgtttg ccctcttgct tgaggatccc     180
gatttcaatt tgccgatcgg gttgaaaatg gaaatagcgt aatgactgta aaaagtacg      240 attcaaatga ggtgcatgct gctctaaata aacaatgtcg gcatccgaaa agcgcaatga     300
agccaactga ttgatttctt ggcgtacttc ctctaataaa tcgctaatgt cttcatcact     360
gcgcacaatc aattcatagc gcacctcaac atccggatac aacgaatgaa cggcctgcat     420
catattgatt ttataggcat caagatccaa taaactgcgg ataaaaagag gagaaaatag     480
gcgatcgctc atgatgatgc catcctttcg ttcggtttca ttcagtcatt acgttagtaa     540
caacgtgttg ctaactttgg gcgaacaata aagtaccctt gtaagtttgt caacttttgt     600 gacaaccta gtcagtcgtt atttggcctt attataatta tggatattga ggggtaagga     660
cgtagtcata acaacaatta cagtactctt gttatctgag ttatgtttgt cacaaagtct     720
tatttacatt tgaccatcat catgcactta cctaaaataa gcccgttgtt tattagggaa     780
gccattatga ttgtcactat cgatatgatt tgtctgcgtc ttgcgccgaa atctatccag     840
gttttactgg tgaaacgctc taatccaaat cggccagatt gtggtaaatg ggcattgcct     900
ggcgggatag tgtatgacga agatatgacc gctcatggtg gagaacctgt cgatgaggat     960
tttgatgcag cgagacgacg tatttgtcgg caaaaagtcc atacttatcc taattttatc    1020
agcgatccgc tggttgatgg caaccccaaa cgcgatccga atggttggag tgtcagtatt    1080
tcccattacg ctttattaaa cccgtggaat gtcaaacaaa tagaagattt tggtatcgac    1140
cccgagcgcg ctaattggtt tgatcttcat actttactca aagaagaaat gccgctggct    1200
tttgatcatg tcgcgcaaat tcagcatgcg tggcaaaaat tacgcgctgc ggttgaatac    1260
acatccgtgg tactattttc attagaaaaa gagttttttag tggcggatat tattgatgcc    1320
tacgccaaat ttggcgtcga agttaatcgc atgaccatta aacgccgctt gatcaatacc    1380 gggtgatcg tcagtaccaa taaatggcc gcatcttgta aaggcaaagg agccaaacca    1440
gccaccgttt atcgtcttgc cagtcatgaa gtcacctatt ttcaaacctg tttacgaggt    1500
```

-continued

```
taactgttcg aaaatcgtgt acagtaggtg atgatgtcaa ttgatgatag gtaggaagca    1560
atgcagatta ttcttgttca tggactctat atgcatggct tggtaatgca tccgcttagt    1620
catcgtctgc ataaattggg ttatcgtact caaaccatta gctacaactc actcgctatc    1680
gatgatgagg ccattttcg ccgccttgac cgatcgctca ctcatgcctc gcctaatgct     1740
ttagtcggac acagtttggg cggattggtg atcaaacgtt atctagaatc gcgcgcaccg    1800
tcctgtgaaa ccctctccca tgtcgtcgcc atcggctcac ctttgcaagg agcttccatt    1860
gtcaataaaa ttgagcaatt aggtttaggg gtggcactag gtaattcagc agaatttggg    1920
ttaaaagaac acgacgacga atcccgctat ccacaaaaat caggcagtat tgcaggaacg    1980 ataccttag  ggctgcgcag cctttactg  cgcgatccac tggactccga tggtaccgtc    2040
acagtagaag aaaccaaaat agctggcatg acagatcata tcgcgatatc caccacttca    2100
tacgagaatg ctgtttaatc attccgttgc cgagcaaatc gaccactttc ttcgttatga    2160
ccgcttccgg cgctaaagcc gtttaaactt cagatgatag tgtacttcgt atcaaaccga    2220
tggtgattga aaacataccc accattcatt cagaataaga cgttgccatc atcgagagctt   2280 tcccatgcaa taaacaatcc gcgactttac gtctggccgc tttaactaaa ttggcaagtg    2340
tctgccgcga tacgctgatg ccgcatagtt aagccagccc cgacaccgc  caacaccccgc   2400 tgacgcgccc tgacgggctt gtctgctccc ggcatccgct tacagacaag ctgtgaccgt    2460
ctccgggagc tgcatgtgtc agaggtttc  accgtcatca ccgaaacgcg cgagacgaaa    2520
gggcctcgtg atacgccat  ttttataggt taatgtcatg ataataatgg tttcttag     2578
```

<210> SEQ ID NO 2
<211> LENGTH: 798
<212> TYPE: DNA
<213> ORGANISM: Vibrio metschnikovii RH530
<220> FEATURE:
<221> NAME/KEY: CDS
<222> LOCATION: (1)..(798)
<223> OTHER INFORMATION: valL1 gene

<400> SEQUENCE: 2

```
atg ttt gtc aca aag tct tat tta cat ttg acc atc atc atg cac tta         48
Met Phe Val Thr Lys Ser Tyr Leu His Leu Thr Ile Ile Met His Leu
 1               5                  10                  15 cct aaa ata agc ccg ttg ttt att agg gaa gcc att atg att gtc act         96
Pro Lys Ile Ser Pro Leu Phe Ile Arg Glu Ala Ile Met Ile Val Thr
             20                  25                  30 atc gat atg att tgt ctg cgt ctt gcg ccg aaa tct atc cag gtt tta        144
Ile Asp Met Ile Cys Leu Arg Leu Ala Pro Lys Ser Ile Gln Val Leu
         35                  40                  45 ctg gtg aaa cgc tct aat cca aat cgg cca gat tgt ggt aaa tgg gca        192
Leu Val Lys Arg Ser Asn Pro Asn Arg Pro Asp Cys Gly Lys Trp Ala
     50                  55                  60 ttg cct ggc ggg ata gtg tat gac gaa gat atg acc gct cat ggt gga        240
Leu Pro Gly Gly Ile Val Tyr Asp Glu Asp Met Thr Ala His Gly Gly
 65                  70                  75                  80 gaa cct gtc gat gag gat ttt gat gca gcg aga cga cgt att tgt cgg        288
Glu Pro Val Asp Glu Asp Phe Asp Ala Ala Arg Arg Arg Ile Cys Arg
                 85                  90                  95 caa aaa gtc cat act tat cct aat ttt atc agc gat ccg ctg gtt gat        336
Gln Lys Val His Thr Tyr Pro Asn Phe Ile Ser Asp Pro Leu Val Asp
            100                 105                 110 ggc aac ccc aaa cgc gat ccg aat ggt tgg agt gtc agt att tcc cat        384
Gly Asn Pro Lys Arg Asp Pro Asn Gly Trp Ser Val Ser Ile Ser His
```

```
                  115                 120                 125
tac gct tta tta aac ccg tgg aat gtc aaa caa ata gaa gat ttt ggt        432
Tyr Ala Leu Leu Asn Pro Trp Asn Val Lys Gln Ile Glu Asp Phe Gly
130                 135                 140 atc gac ccc gag cgc gct aat tgg ttt gat ctt cat act tta ctc aaa        480
Ile Asp Pro Glu Arg Ala Asn Trp Phe Asp Leu His Thr Leu Leu Lys
145                 150                 155                 160 gaa gaa atg ccg ctg gct ttt gat cat gtc gcg caa att cag cat gcg        528
Glu Glu Met Pro Leu Ala Phe Asp His Val Ala Gln Ile Gln His Ala
                165                 170                 175 tgg caa aaa tta cgc gct gcg gtt gaa tac aca tcc gtg gta cta ttt        576
Trp Gln Lys Leu Arg Ala Ala Val Glu Tyr Thr Ser Val Val Leu Phe
            180                 185                 190 tca tta gaa aaa gag ttt tta gtg gcg gat att att gat gcc tac gcc        624
Ser Leu Glu Lys Glu Phe Leu Val Ala Asp Ile Ile Asp Ala Tyr Ala
        195                 200                 205 aaa ttt ggc gtc gaa gtt aat cgc atg acc att aaa cgc cgc ttg atc        672
Lys Phe Gly Val Glu Val Asn Arg Met Thr Ile Lys Arg Arg Leu Ile
    210                 215                 220 aat acc ggg gtg atc gtc agt acc aat aaa atg gcc gca tct tgt aaa        720
Asn Thr Gly Val Ile Val Ser Thr Asn Lys Met Ala Ala Ser Cys Lys
225                 230                 235                 240 ggc aaa gga gcc aaa cca gcc acc gtt tat cgt ctt gcc agt cat gaa        768
Gly Lys Gly Ala Lys Pro Ala Thr Val Tyr Arg Leu Ala Ser His Glu
                245                 250                 255 gtc acc tat ttt caa acc tgt tta cga ggt                                798
Val Thr Tyr Phe Gln Thr Cys Leu Arg Gly
            260                 265

<210> SEQ ID NO 3
<211> LENGTH: 266
<212> TYPE: PRT
<213> ORGANISM: Vibrio metschnikovii RH530

<400> SEQUENCE: 3

Met Phe Val Thr Lys Ser Tyr Leu His Leu Thr Ile Ile Met His Leu
1               5                   10                  15

Pro Lys Ile Ser Pro Leu Phe Ile Arg Glu Ala Ile Met Ile Val Thr
            20                  25                  30

Ile Asp Met Ile Cys Leu Arg Leu Ala Pro Lys Ser Ile Gln Val Leu
        35                  40                  45

Leu Val Lys Arg Ser Asn Pro Asn Arg Pro Asp Cys Gly Lys Trp Ala
    50                  55                  60

Leu Pro Gly Gly Ile Val Tyr Asp Glu Asp Met Thr Ala His Gly Gly
65                  70                  75                  80

Glu Pro Val Asp Glu Asp Phe Asp Ala Ala Arg Arg Ile Cys Arg
                85                  90                  95

Gln Lys Val His Thr Tyr Pro Asn Phe Ile Ser Asp Pro Leu Val Asp
            100                 105                 110

Gly Asn Pro Lys Arg Asp Pro Asn Gly Trp Ser Val Ser Ile Ser His
        115                 120                 125

Tyr Ala Leu Leu Asn Pro Trp Asn Val Lys Gln Ile Glu Asp Phe Gly
    130                 135                 140

Ile Asp Pro Glu Arg Ala Asn Trp Phe Asp Leu His Thr Leu Leu Lys
145                 150                 155                 160

Glu Glu Met Pro Leu Ala Phe Asp His Val Ala Gln Ile Gln His Ala
                165                 170                 175
```

-continued

```
Trp Gln Lys Leu Arg Ala Ala Val Glu Tyr Thr Ser Val Val Leu Phe
            180                 185                 190

Ser Leu Glu Lys Glu Phe Leu Val Ala Asp Ile Ile Asp Ala Tyr Ala
        195                 200                 205

Lys Phe Gly Val Glu Val Asn Arg Met Thr Ile Lys Arg Arg Leu Ile
    210                 215                 220

Asn Thr Gly Val Ile Val Ser Thr Asn Lys Met Ala Ala Ser Cys Lys
225                 230                 235                 240

Gly Lys Gly Ala Lys Pro Ala Thr Val Tyr Arg Leu Ala Ser His Glu
                245                 250                 255

Val Thr Tyr Phe Gln Thr Cys Leu Arg Gly
            260                 265
```

<210> SEQ ID NO 4
<211> LENGTH: 555
<212> TYPE: DNA
<213> ORGANISM: Vibrio metschnikovii RH530
<220> FEATURE:
<221> NAME/KEY: CDS
<222> LOCATION: (1)..(555)
<223> OTHER INFORMATION: valL2 gene

<400> SEQUENCE: 4

```
atg cag att att ctt gtt cat gga ctc tat atg cat ggc ttg gta atg      48
Met Gln Ile Ile Leu Val His Gly Leu Tyr Met His Gly Leu Val Met
1               5                   10                  15 cat ccg ctt agt cat cgt ctg cat aaa ttg ggt tat cgt act caa acc      96
His Pro Leu Ser His Arg Leu His Lys Leu Gly Tyr Arg Thr Gln Thr
            20                  25                  30 att agc tac aac tca ctc gct atc gat gat gag gcc att ttt cgc cgc     144
Ile Ser Tyr Asn Ser Leu Ala Ile Asp Asp Glu Ala Ile Phe Arg Arg
        35                  40                  45 ctt gac cga tcg ctc act cat gcc tcg cct aat gct tta gtc gga cac     192
Leu Asp Arg Ser Leu Thr His Ala Ser Pro Asn Ala Leu Val Gly His
    50                  55                  60 agt ttg ggc gga ttg gtg atc aaa cgt tat cta gaa tcg cgc gca ccg     240
Ser Leu Gly Gly Leu Val Ile Lys Arg Tyr Leu Glu Ser Arg Ala Pro
65                  70                  75                  80 tcc tgt gaa acc ctc tcc cat gtc gtc gcc atc ggc tca cct ttg caa     288
Ser Cys Glu Thr Leu Ser His Val Val Ala Ile Gly Ser Pro Leu Gln
                85                  90                  95 gga gct tcc att gtc aat aaa att gag caa tta ggt tta ggg gtg gca     336
Gly Ala Ser Ile Val Asn Lys Ile Glu Gln Leu Gly Leu Gly Val Ala
            100                 105                 110 cta ggt aat tca gca gaa ttt ggg tta aaa gaa cac gac gac gaa tcc     384
Leu Gly Asn Ser Ala Glu Phe Gly Leu Lys Glu His Asp Asp Glu Ser
        115                 120                 125 cgc tat cca caa aaa tca ggc agt att gca gga acg ata cct tta ggg     432
Arg Tyr Pro Gln Lys Ser Gly Ser Ile Ala Gly Thr Ile Pro Leu Gly
    130                 135                 140 ctg cgc agc ctt tta ctg cgc gat cca ctg gac tcc gat ggt acc gtc     480
Leu Arg Ser Leu Leu Leu Arg Asp Pro Leu Asp Ser Asp Gly Thr Val
145                 150                 155                 160 aca gta gaa gaa acc aaa ata gct ggc atg aca gat cat atc gcg ata     528
Thr Val Glu Glu Thr Lys Ile Ala Gly Met Thr Asp His Ile Ala Ile
                165                 170                 175 tcc acc act tca tac gag aat gct gtt                                  555
Ser Thr Thr Ser Tyr Glu Asn Ala Val
            180                 185
```

-continued

```
<210> SEQ ID NO 5
<211> LENGTH: 185
<212> TYPE: PRT
<213> ORGANISM: Vibrio metschnikovii RH530

<400> SEQUENCE: 5

Met Gln Ile Ile Leu Val His Gly Leu Tyr Met His Gly Leu Val Met
 1               5                  10                  15

His Pro Leu Ser His Arg Leu His Lys Leu Gly Tyr Arg Thr Gln Thr
            20                  25                  30

Ile Ser Tyr Asn Ser Leu Ala Ile Asp Asp Glu Ala Ile Phe Arg Arg
        35                  40                  45

Leu Asp Arg Ser Leu Thr His Ala Ser Pro Asn Ala Leu Val Gly His
    50                  55                  60

Ser Leu Gly Gly Leu Val Ile Lys Arg Tyr Leu Glu Ser Arg Ala Pro
65                  70                  75                  80

Ser Cys Glu Thr Leu Ser His Val Val Ala Ile Gly Ser Pro Leu Gln
                85                  90                  95

Gly Ala Ser Ile Val Asn Lys Ile Glu Gln Leu Gly Leu Gly Val Ala
            100                 105                 110

Leu Gly Asn Ser Ala Glu Phe Gly Leu Lys Glu His Asp Asp Glu Ser
        115                 120                 125

Arg Tyr Pro Gln Lys Ser Gly Ser Ile Ala Gly Thr Ile Pro Leu Gly
    130                 135                 140

Leu Arg Ser Leu Leu Leu Arg Asp Pro Leu Asp Ser Asp Gly Thr Val
145                 150                 155                 160

Thr Val Glu Glu Thr Lys Ile Ala Gly Met Thr Asp His Ile Ala Ile
                165                 170                 175

Ser Thr Thr Ser Tyr Glu Asn Ala Val
            180                 185
```